(12) United States Patent
Rickwood

(10) Patent No.: US 6,562,623 B1
(45) Date of Patent: May 13, 2003

(54) METHOD FOR INTRODUCING A SUBSTANCE INTO A CELL

(75) Inventor: David Rickwood, Colchester (GB)

(73) Assignee: Immunoporation Ltd (GB)

( * ) Notice: Subject to any disclaimer, the term of this patent is extended or adjusted under 35 U.S.C. 154(b) by 0 days.

(21) Appl. No.: 10/031,903

(22) PCT Filed: Jul. 21, 2000

(86) PCT No.: PCT/GB00/02826

§ 371 (c)(1),
(2), (4) Date: Apr. 30, 2002

(87) PCT Pub. No.: WO01/05994

PCT Pub. Date: Jan. 25, 2001

(30) Foreign Application Priority Data

Jul. 21, 1999 (GB) .............................................. 9917130
Feb. 18, 2000 (GB) .............................................. 0003893

(51) Int. Cl.⁷ .............................................. C12N 15/64
(52) U.S. Cl. .................... 435/455; 435/173.5; 435/375; 435/285.1
(58) Field of Search .............................. 435/455, 173.5, 435/375, 285.1

(56) References Cited

FOREIGN PATENT DOCUMENTS

| WO | WO91/00915 | 1/1991 |
|---|---|---|
| WO | WO99/31262 | 6/1999 |

OTHER PUBLICATIONS

"Transformation of Acetobacter Polyoxogenes with Plasmid DNA by Electroporation," Tayama, Kenji et al, Bioscience Biotechnology and Biochemistry, vol. 58, No. 5, 1994, pp 974–975.

"Artificial Cavitation Nuclei Significantly Enhance Acoustically Induced Cell Transfection," Greenleaf, William J. et al, Ultrasound in Medicine and Biology, vol. 24, No. 4, 1998, pp 587–595.

"The Mechanism of Osmotic Transfection of Avian Embryonic Erythrocytes: Analysis of a System for Studying Developmental Gene Expression," Lieber, Michael R. et al, Journal of Cell Biology, vol. 105, Sep. 1987, pp 1055–1065.

"Cytoplasmic Loading of Dyes, Protein and Plasmid DNA Using an Impact–Mediated Procedure," Biotechniques, vol. 17, No. 6, 1994, pp 1118–1122.

Primary Examiner—James Ketter
(74) Attorney, Agent, or Firm—Carmody & Torrance LLP

(57) ABSTRACT

Provided is a method for introducing a substance into a cell, which method comprises: (a) generating one or more bubbles of a gas in a liquid medium comprising the cell, the bubbles being capable of forming a hole in the surface of the cell when one or more bubbles interact with the cell; and (b) introducing the substance into the cell.

16 Claims, No Drawings

METHOD FOR INTRODUCING A SUBSTANCE INTO A CELL

The present invention relates to a method for introducing a substance into a cell, and in particular to an efficient transfection method involving a low incidence of cell-death. The invention also relates to a kit for introducing a substance into a cell.

The introduction of foreign substances, such as foreign DNA, into cells is termed transfection. This technique has recently proved to be one of the most important techniques in molecular biology, particularly in relation to genetic engineering and protein engineering. The technique has allowed foreign DNA to be expressed in cells. This is of scientific interest in studying gene transcription and has a wide range of commercial applications involving expressing commercially useful gene products in convenient types of cell. More recently there has been interest in introducing both proteins and drugs into living cells without damaging the cells. A significant problem to be overcome when developing such techniques is the general imperviousness of the cell membrane. The cell membrane is normally impervious to even small molecules, unless they are very lipophilic. Even short-term damage to the cell membrane to render it more permeable tends to result in cell-death. This is a particular problem associated with electroporation, discussed below.

A number of methods have been devised for transfecting cells with foreign DNA or other substances. Early methods involved binding DNA to particles such as diethylaminoethyl (DEAE) cellulose or hydroxyapatite and adding pretreated cells which are capable of taking up particles containing DNA. These early methods are very inefficient, the level of transfection achievable being very low.

More recently methods have been developed which make use of liposomes loaded with DNA that can be fused with cells. A further technique involves subjecting cells to an electric shock which causes the formation of holes in the cells. This method is termed electroporation.

In Biotechniques, Vol. 17 No. 6 1994, page 118–1125, Clarke et al. disclose a method for introducing dyes, proteins and plasmid DNA into cells using an impact-mediated procedure. In this method, compressed gas is used to propel glass beads dispersed as a uniform aerosol onto adherent cells growing on a culture substratum. The impact of beads on the cells creates plasma membrane wounds. Molecules such as dyes, proteins and plasmid DNAs diffuse from the extracellular environment directly into the cytoplasmic compartment of the cell through the wounds.

In *Nucleic Acids Research*, Vol. 18, No. 21, 1990, p.6464, the effect of the osmolarity of the transfection medium is studied in relation to electroporation methods. It was reported that the optimum osmolarity of the transfection medium for transfection by electroporation is around 300 mOsm.

A significant problem associated with the above treatments is that they are very inefficient. In addition, a large proportion of the cells are killed by the above treatments. Moreover, the treatments are not selective. In fact, no methods are presently available for the selective transfection of cells. Furthermore, in the method of Clarke et al, only a limited number of cells can be transfected in a single treatment.

In Animal Cell Culture: A Practical Approach, (edited by R. I. Freshney, Second Ed., 1992, page 56–57, IRL Press, OUP) a method of oxygenating a cell culture is discussed. The method involves sparging. This is the bubbling of gas through a liquid medium comprising the culture. The reference states that gas bubbles having a high surface energy may damage animal cell membranes if not properly controlled.

An object of the present invention is to overcome the above drawbacks and to provide an efficient method of transfection. Accordingly, the present invention provides a method for introducing a substance into a cell, which method comprises:

(a) generating bubbles of a gas in a liquid medium comprising the cell, the bubbles being capable of forming a hole in the surface of the cell when one or more bubbles interact with the cell; and (b) introducing the substance into the cell.

In the present invention the bubbles are capable of forming a hole in the surface of the cell. This means that the dimensions of the bubbles, and their composition (in terms of both the liquid medium and the gas of the bubbles) are sufficient to enable the bubbles to form holes in the cell surface.

In the present invention, any method can be used to generate the bubbles of gas in the liquid medium containing the cells, provided that the dimensions of the bubbles are controlled such that the bubbles are capable of forming transient holes in the cell (in particular when interacting with the cell surface). The formation of holes in the cell surface using bubbles is termed aeroporation in the context of the present application. Preferably, the dimensions of the bubbles are comparable to the dimensions of the cell. For example, a preferred bubble radius ranges from approximately one third times the radius of the cell to five times the radius of the cell.

In one embodiment, the bubbles of gas are generated by introducing a gas into the liquid medium in a sparging process. Typically, but not exclusively, sparging involves the passage of gas through a porous element (e.g. a filter) which is in contact with the liquid medium. The porous element ensures that the gas enters the liquid evenly across a given area of the liquid, thus forming small bubbles extending evenly throughout the volume of the liquid.

In another embodiment, the bubbles of gas may be generated by a chemical, or an electrochemical reaction, such as by the decomposition of hydrogen peroxide contained in the liquid medium.

In a further embodiment, the bubbles of gas may be generated in the liquid medium by a depressurisation process. Depressurisation typically involves reducing the pressure to which the liquid medium is exposed, such that the solubility of the dissolved gas is reduced, causing the formation of bubbles in the liquid. Without being bound by theory, it is believed that the cells in the liquid medium act as nuclei for the formation of the bubbles of gas. This embodiment thereby advantageously allows the formation of bubbles in close proximity with the cells, increasing the efficiency of transfection.

The dissolved gas may be gas that is present in the liquid medium naturally under ambient conditions, or in an alternative embodiment gas may be dissolved in the liquid medium prior to carrying out the present method. Gas may be dissolved in the liquid medium by any means, such as by controlling the temperature and/or pressure, or preferably by increasing the pressure. The type of gas used is not especially limited, but it is preferred that the gas used is air, or another gas that is soluble in an aqueous medium. The rate of generation of the bubbles of gas and the size of the bubbles may be controlled by varying the rate and extent of the decrease of the pressure.

The extent of foam formation on the surface of the liquid is preferably controlled by introducing a foam-controlling agent. The foam controlling agent used in the present invention is not especially limited and may include any known foam controlling agent, such as a commercially available fatty acid.

In the present methods, without being bound by theory, it is believed that gas bubbles having a sufficiently small radius have sufficient surface energy (or surface tension) that on interacting with the cells (such as contacting the cells and in particular, bursting when in contact with or in close proximity to the cells) a hole is formed in the cell surface. The hole in the cell surface may be a rip or tear in the cell membrane and may also include a hole formed by entirely removing a portion of the cell membrane. The hole provides access to the inside of the cell, allowing the substance to enter the internal parts of the cell, such as the cytoplasm.

There is no significant decrease in the viability of the cells, even though holes are formed in the cell surface. The holes formed in the cells are transient, remaining open for a sufficient time to allow the influx of macromolecules into the cell, but re-sealing before the viability of the cell is compromised. For instance, using the method of the present invention, cell-death is generally less than 25% and often less than 5%. On the other hand, if electroporation is used cell-death can sometimes be as high as 90%.

The step (a) of the present method is carried out in a liquid medium. In the present context this is also termed a transfection medium. The ions present in the transfection medium are not particularly limited, provided that they do not inhibit transfection and can be tolerated by the cells. A transfection medium having an appropriate osmolarity may be formulated using 10 times concentrated Earle's balanced salt solution (EBSS) (Earle, W. R., 1934, Arch. Exp. Zell. Forsch., Vol. 16, p. 116) containing nutrient factors as a base, and diluting as required.

It is preferred that the substance to be introduced into the cell is contained within the transfection medium. In this preferred embodiment the substance is introduced into the cell in a step which is substantially simultaneous with the step of generating the bubbles of gas in the transfection medium. However, it is also possible that the substance can be contacted with the cell after the bubbles of gas have been generated in the transfection medium and the transient hole has been created in the cell surface, provided that the substance is introduced before the transient hole in the cell surface re-seals.

The liquid medium employed is not particularly limited and is preferably an aqueous medium. The medium may comprise a buffer or a cell culture medium. The concentration of the substance in the medium is not particularly limited and may be selected according to the quantity of substance which is required to be introduced into the cell. A convenient concentration is $0.2–10\times10^{-8}$ M, more preferably $0.75–1.25\times10^{-8}$ M.

The gas used in the present method is not particularly limited provided that it is capable of forming bubbles which are able to interact with cells to form transient holes in the cell surface. Typically the gas is air, however oxygen and nitrogen can also be used. In addition, $CO_2$ can also be used, particularly if it is desirable to maintain the pH of the liquid medium at a specific level. When $CO_2$ is used it is generally employed as a 5–7% vol. concentration in another gas, such as air. In the embodiment employing depressurisation, the gas should be at least sparingly soluble in the liquid medium under the conditions at which the method is carried out.

The depth of the liquid medium in which the bubbles of gas are generated is not especially limited. Where the bubbles of gas are generated by introducing a gas into the liquid medium by sparging, transfection is not particularly sensitive to the gas flow rate per volume of liquid medium, but is more sensitive to the gas flow rate per area of the porous element through which the gas is passed into the liquid. In any case, the depth of the liquid medium is typically 10 cm or less.

In the embodiments employing sparging to introduce the gas into the liquid medium, typically, for each square centimetre of cross sectional area of the liquid (e.g. of the porous element area), a gas flow of 0.1 l/min or more is employed. More preferably, a flow rate of 0.125–0.5 l/min is employed, (at standard temperature and pressure).

Where the bubbles of gas are generated in the liquid medium by a depressurisation process, transfection is more sensitive to pressure, and in particular the length of time the liquid medium and the cells are exposed to an increased pressure.

Transfection can be carried out under widely varying conditions. Where the bubbles of gas are generated by introducing a gas into the liquid by sparging, transfection is carried out at room temperature (ambient temperature) such as from 15–30° C. and more preferably from 20–25° C. In this embodiment, transfection is carried out at $1\times10^4$ Pa (0.1 Barr) or more, e.g. at atmospheric pressure ($1\times10^5$ Pa, 1 Barr). Preferably the method is carried out at a pressure of from $1\times10^4$ Pa (0.1 Barr) to atmospheric pressure, or at from $1\times10^4–1\times10^5$ Pa (0.1–1 Barr), more preferably at $4\times10^4–8\times10^4$ Pa (0.4–0.8 Barr), although it can be carried out at elevated pressure if desired, e.g. at atmospheric pressure or above ($1\times10^5$ Pa (1 Barr) or above).

Where the bubbles of gas are generated in the liquid medium by a depressurisation process, the gas may be present naturally in the medium, or the natural gas content of the liquid medium may be increased by applying pressure and/or by pre-dissolving gas in the liquid medium. In this embodiment transfection is preferably carried out at a constant temperature, typically room temperature, such as from 5–30° C., preferably from 15–30° C. The method typically involves holding the liquid medium at a starting pressure for a period of time, and then reducing the pressure to form bubbles. The starting pressure may be selected to facilitate initial dissolution of gas in the liquid medium if desired. The starting pressure is usually $5\times10^6$ Pa (50 Barr) or less and preferably from $2\times10^6–3\times10^6$ Pa (20–30 Barr). The gas is preferably held at the starting pressure for 30 min. or less, preferably from 1–20 min, more preferably from 5–20 min. and most preferably for about 10 min. This time can be varied, if desired, to alter the quantity of gas initially dissolved in the liquid medium. The pressure is typically lowered to atmospheric pressure ($1\times10^5$ Pa, 1 Barr). The pressure is preferably lowered rapidly, such as by sudden de-compression, e.g. by exposing the isolated system to the atmosphere. This may be effected by (for example) simply opening a valve or tap connected to the container comprising the liquid medium.

The presence of the gas in the transfection medium can be maintained for as long as necessary, and may be determined according to the conditions employed for transfection, such as the gas used, the temperature, the pressure, the method of generation of bubbles used, as well as the type of cell and substance to be transfected.

The generation of the bubbles of gas may take place continuously for a single period of time or may take place in two or more pulses separated by intervals in which substantially no bubbles are generated. In one embodiment, the generation of bubbles of gas in the transfection medium takes place for a period of 10 minutes or more at standard temperature and pressure, depending on the level of transfection required. More preferably, generation of bubbles of gas takes place for 10–60 mins, most preferably from 20–40 mins.

In another embodiment, the bubbles of gas are generated in two or more pulses. Preferably, generation of bubbles of gas takes place in short pulses over the duration of the transfection method. Pulses may typically be from 1–10 s in length. For example, pulses may be from 1–5 s in length, separated by a period of similar length during which no gas generation takes place. Any means may be used for controlling the duration of the pulses. Typically the duration of the pulses may be controlled by a programmable means. Such a means may, for example, include a programmable timer used to control the activity of the means for generating the bubbles of gas. The timer may, for instance, control the opening and closing of a valve attached to a gas source, or may control a means for varying the pressure above the liquid medium.

The pulsing method can be applied to embodiments using sparging to generate gas bubbles in the liquid medium, as well as to embodiments using depressurisation, chemical, or electrochemical means to generate the gas bubbles.

The concentration of the cells in the liquid medium is not particularly limited. However, generally the most efficient transfection is observed when the cell concentration is from 10,000–2,000,000 cells/ml, more preferably 100,000–1,000,000 cells/ml and most preferably 100,000–500,000 cells/ml.

The substance to be introduced can be any substance. Preferably the substance is a substance not normally able to cross the cell membrane. It is thus preferred that the substance to be introduced into the cell is a hydrophilic substance, however the substance may also be hydrophobic. Any biological molecule or any macromolecule can be introduced into the cell. The substance generally has a molecular weight of 100 daltons or more. In a more preferred embodiment, the substance is nucleic acid such as DNA or RNA (e.g. a gene, a plasmid, a chromosome, an oligonucleotide, a nucleotide sequence, or a ribozyme) or a fragment thereof, or an expression vector. Additionally, the substance may be a bio-active molecule such as a protein, a polypeptide, a peptide, an amino acid, a hormone, a polysaccharide, a dye, or a pharmaceutical agent such as drug.

The cells to which the method of the present invention can be applied are not particularly limited. It is preferred that the cell against which the method is employed is an animal cell, preferably mammalian cells such as human cells. However, the method can also be employed to treat cells with cell walls, such as plant cells, fungal cells and bacteria. In this latter embodiment, it is preferred that the method is carried out on a protoplast derived from the cell.

Using the method of the present invention, a population of cells can be transfected. These cells may, for instance, be in the form of a cell suspension or may be adherent cells on a solid surface. The method may also be employed to treat a cell population containing a plurality of cell types.

The present invention also provides a kit for introducing a substance into a cell, which kit comprises;

(i) a means for generating bubbles of a gas in a liquid, wherein the bubbles have dimensions substantially sufficient to form a hole in the surface of the cell when one or more bubbles interact with the cell; and (ii) a liquid medium.

The means for generating bubbles of a gas in a liquid is not particularly limited, provided that it is suitable for producing a bubble of dimensions sufficient to form a hole in the surface of the cell when the bubble interacts with the cell (in particular, the cell surface). In one embodiment a means such as a conventional sparging means can be employed. A typical sparging means includes a porous element, such as a filter which is porous to a gas, but which is substantially impervious to the liquid medium during sparging. The filter thus keeps the transfection medium contained, whilst allowing the gas to pass through into the liquid. A useful device for carrying out the present method is an AutoPrep® (manufactured by Hybaid, Ashford, Middlesex, UK).

Producing bubbles having the desired dimensions in sufficient quantity to provide efficient transfection can be problematic for some cell types. In these cases, known filters, such as those normally used for sparging, produce bubbles which are often too large to effect transfection, except in the case of the largest types of cell. However, when filters are constructed with smaller pores to produce smaller bubbles, it is difficult to pass a sufficient volume of gas through the filter to effect efficient transfection. Accordingly the present invention also provides a filter system which solves this problem and can produce bubbles having desired dimensions in sufficient volume to allow efficient transfection.

Thus, in a further aspect of the present invention, there is provided a filter system for passing a gas through a liquid medium comprising a cell, which filter system comprises a filter layer formed from glass, a filter layer formed from polypropylene and a filter layer formed from cellulose nitrate. The order of these layers is not especially limited.

The filter system of the present invention is particularly suitable for use in the transfection method of the present invention, since it is capable of forming bubbles of optimum dimensions for forming holes in the surface of a cell. The order of the layers is not particularly limited, and the glass layer, the polypropylene layer or the cellulose nitrate layer may be the uppermost layer (in closest proximity to, or in contact with, the liquid medium). The filter system, has at least three layers, as described above, but may also have one or more further layers. Thus, the filter system may comprise three, four five or more layers in total. The order of these further layers is not especially limited.

When the filter system of the present invention comprises one or more further layers, the materials from which the further layers are formed are not particularly limited. Typically the material from which each further layer is formed is independently selected from glass, polypropylene, cellulose nitrate and paper. In a preferred embodiment, the filter system comprises a further layer formed from cellulose nitrate. When the filter system comprises a cellulose nitrate layer, it is preferred that the cellulose nitrate layer is flanked both above and below by a polypropylene layer.

A particularly preferred filter system of the present invention comprises filter layers in the following order, starting from the uppermost layer (the layer closest to the liquid medium): polypropylene/cellulose nitrate/glass/cellulose nitrate/polypropylene. A further preferred filter system of the present invention comprises filter layers in the following order: glass/polypropylene/cellulose nitrate/polypropylene.

In the filter system of the present invention, it is preferred that the glass filter layer is formed from glass fibre, such as glass microfibre.

The filter system of the present invention typically comprises a grid above the uppermost filter layer, to increase the mechanical strength of the filter system. The grid may be formed from any substance, but is preferably formed from metal. The metal grid is preferably a steel grid, such as a stainless steel grid. As mentioned above, the grid serves to provide mechanical strength to the filter system. This may be desirable when higher pressures are employed, such as at atmospheric pressure or above.

The pore size and area of the filter layers is not especially limited, provided that the filter system is sufficiently permeable to the gas employed to produce bubbles of the required dimensions. Thus, any standard commercially available filters can be used, such as glass (e.g. glass microfibre), polypropylene, cellulose nitrate and paper filters having standard pore sizes. Typically, polypropylene and glass filters having a pore size of 10 $\mu$m or more are employed, and cellulose nitrate filters having a pore size of 8 $\mu$m or more are employed.

In another embodiment, a depressurisation means may be employed for generating bubbles of gas in the liquid. A typical depressurisation means comprises a sealable chamber for holding the liquid medium in which the pressure may be varied and a means for varying the pressure in the chamber. The means for varying the pressure is typically a compressor (such as a cylinder of compressed gas) connected to the sealed chamber, for increasing the pressure in the chamber and/or compressing gas in the chamber. The size and nature of the sealed chamber is not particularly limited provided it is capable of containing the liquid and withstanding a pressure difference between the inside and outside of the chamber. The means for varying the pressure is not particularly limited provided that it is capable of generating a pressure difference between the inside and outside of the chamber.

The means for generating bubbles of gas in the liquid may be controlled by a programmable means. Typically a programmable timer is used to control the activity of the depressurisation or sparging means.

In a further aspect, the present invention provides an apparatus for generating a gas in a liquid medium comprising a cell, which apparatus comprises, (i) a container for holding the liquid comprising the cell; and (ii) a means for generating bubbles of gas in the container, which means comprises a filter system and/or a depressurisation means, as defined above.

The present invention also provides use of the above apparatus in a transfection method.

The container holding the liquid is not especially limited, and may be formed from glass or plastics or another convenient material. Where the bubbles of gas are generated in a sparging process using a filter system, it is preferred that the cross-sectional area of the container is substantially the same as the cross-sectional area of the filter layers of the filter system. This has the advantage of distributing the gas evenly throughout the liquid medium.

In one embodiment the apparatus is arranged with a filter system directly below the container holding the liquid, such that in use, the gas passes through the filter system from below and enters the liquid from below, passing out at the upper surface of the liquid. This is termed a vertical configuration. The apparatus is not limited to the vertical configuration, and the gas may be made to pass through the liquid in a horizontal configuration, or any alternative configuration, if desired.

In another embodiment, the container holding the liquid is sealable such that the pressure may be varied, the container being connected to a means for varying the pressure in the container.

In a further aspect of the present invention, there is provided a kit for introducing a substance into a cell, which kit comprises;

(i) a filter system for passing a gas through a liquid medium comprising a cell, which filter system is as defined above; and (ii) optionally a liquid medium.

The present invention also provides use of a gas in the form of bubbles in a liquid medium, to introduce a substance into a cell, wherein the bubbles have dimensions sufficient to form a hole in the surface of the cell when one or more bubbles interact with the cell.

The methods, filter system, apparatus, kits and uses of the present invention can be employed in non-medical applications, such as in life-sciences applications, as well as in medical applications.

Life sciences applications in which the present invention can be particularly useful include the introduction of specific genes into viable cells for expression and for the analysis of the effect of gene products on the metabolism of cells. Such applications also include the introduction of biologically active proteins into viable cells to study their effects on the cells with regard to the metabolism and morphology of the cells. These applications also extend to the introduction of pharmacologically important compounds into cells, where the cell membrane is normally impervious to such compounds.

Medical applications in which the present invention can be particularly usefull include all applications which are not life sciences applications as defined above, and specifically include gene therapy and the targeted introduction of new genes into specific immunologically defined cell populations with deleted or defective genes. Such applications also include the introduction of genes controlling endocrine functions, such as hormone synthesis and secretion, into epidermal cell populations. The targeted permeabilisation of tumour cells for enhanced chemotherapy procedure is also included in these applications. In particular, the present invention may be employed in gene therapy to great advantage. Additionally, the invention may be used to introduce antisense RNA into specific cell types.

In comparison to known methods, the present method is very efficient. The efficiency of transfection depends upon the length of time during which gas generation is carried out, and the method of generation. In some circumstances, such as when generating gas bubbles by depressurisation, an efficiency of 80% or more, 90% or more or even approximately 100% can be achieved.

The invention will now be further described, by way of example only, with reference to the following specific embodiments.

EXAMPLES

Cells

HL-60 cells were cultured in RPMI 1640 medium (Imperial Labs, Andover, UK) containing 10% foetal calf serum (FCS) (Gibco, BRL, USA).

Calculation of the Amount of Transfection Agent

It is important to determine the required concentration of the agent that is to be transfected into the cell. Macromolecules enter cells by an osmotically enhanced diffusion process and typical concentrations used are from $0.2$–$10 \times 10^{-8}$ M. Whilst it is not usually necessary to know the exact concentration, the concentration is preferably controlled within a range which is not excessively concentrated or dilute, so that the correct quantity of substance is transfected into the cell.

A useful relationship in determining concentration is that the molecular weight of any molecule expressed in $\mu$g/ml corresponds to a $1 \times 10^{-3}$ M concentration. For instance, it can be assumed when calculating the molecular weight of DNA, that the molecular weight of a base pair is 600. Hence a 5 kb DNA vector has a molecular weight of $3 \times 10^{-6}$ and so a solution of 30 mg/ml of this vector has a concentration of $1 \times 10^{-8}$ M.

Example 1

Transfection Using an AutoPrep® (Programmed Pulsing)

HL-60 cells were suspended in an aqueous medium comprising EBSS and having an osmolarity of approximately 300 mOsm. The medium contained approximately 500,000 cells/ml and either fluorescently labelled bovine serum albumin (FITC-BSA) or rhodamine-dextran, at a concentration of 3.0 $\mu$g/ml. The suspension of HL-60 cells was transferred to an AutoPrep® machine (Hybaid, Ashford, Middlesex, UK). Atmospheric air was passed through the cell suspension using the AutoPrep® at room temperature (in this case 15–20° C.) at a pressure of approximately 1 Barr (atmospheric pressure). A flow rate of from 2–8 l/min was used and passaging of the air was allowed to continue for 1 hour, using pulses of approximately 1 s duration, occurring every other second.

Analysis of Transfected Suspension Cells (i) Confocal Microscopy

This operation needs to be performed using as little illumination as possible, to prevent photo-bleaching.

The transfected cells were washed twice with PBS (phosphate buffered saline). The cells (approx. $1 \times 10^4$ in number) were re-suspended in 20 $\mu$l PBS and placed in the wells of a poly-L-lysine coated microscope slide. The cells were then allowed to settle for 20 mins.

The PBS was then gently removed and PFA (paraformaldehyde) was added (4%, 20 $\mu$l). The cells were left to be fixed for 20 mins. Then, the PFA was gently removed and 15 $\mu$l of DABCO (1,4-diazabicyclo[2,2,2] octane) was added. A coverslip was placed over the cells and sealed with grease.

The analysis was performed under a microscope according to standard confocal microscopy techniques. The HL-60 cells transfected with FITC-BSA and rhodamine-dextran exhibited clear fluorescence present inside the cells, not at the cell surface. Thus the cells were successfully transfected. Approximately 50–65% transfection was achieved, with cell death being approximately 10–15%.

(ii) Flow Cytometry

This operation must also be carried out using as little illumination as possible to prevent photo-bleaching. At least 10,000 cells are required for this procedure, an optimum number is 100,000–200,000. A sample of untransfected cells is also required for comparison. The transfected HL-60 cells were washed with 0.2 $\mu$l of filtered PBS using a microcentrifuge set at low speed. After the final wash the cells were re-suspended in 100 $\mu$l PBS. Analysis was carried out using standard flow cytometry methods. Cells transfected with FITC-BSA and rhodamine-dextran showed a clear increase in peal channel and mean over control cells, indicating that they were fluorescent and had thus been transfected.

Example 2

Transfection Using a Filter System of the Present Invention

HL-60 cells were suspended in an aqueous medium comprising EBSS and having an osmolarity of approximately 300 mOsm. The medium contained approximately 500,000 cells/mil and pEGFP-C1 vector, at a concentration of 3.0 $\mu$g/mnl. The suspension of HL-60 cells was transferred to an apparatus comprising a filter system having the following composition: steel mesh/glass microfibre/polypropylene/cellulose nitrate/polypropylene. Atmospheric air was passed through the cell suspension using the filter system in a vertical configuration, at room temperature (in this case 15–20° C.) at a pressure of from $1 \times 10^4$–$8 \times 10^4$ Pa (0.1–0.8 Barr). A flow rate of from 2–11 l/min was used and passaging of the air was allowed to continue for 45 min.

Analysis of Transfected Suspension Cells (i) Confocal Microscopy

This operation needs to be performed using as little illumination as possible, to prevent photo-bleaching.

The transfected cells were washed twice with PBS (phosphate buffered saline). The cells (approx. $1 \times 10^4$ in number) were re-suspended in 20 $\mu$l PBS and placed in the wells of a poly-L-lysine coated microscope slide. The cells were then allowed to settle for 20 mins.

The PBS was then gently removed and PFA (paraformaldehyde) was added (4%, 20 $\mu$l). The cells were left to be fixed for 20 mins. Then, the PFA was gently removed and 15 $\mu$l of DABCO (1,4-diazabicyclo[2,2,2] octane) was added. A coverslip was placed over the cells and sealed with grease.

The analysis was performed under a microscope according to standard confocal microscopy techniques. The HL-60 cells transfected with pEGFP-C1 vector exhibited clear fluorescence present inside the cells, not at the cell surface. Thus the cells were successfully transfected. Approximately 50–65% transfection was achieved, with cell death being approximately 10–15%.

(ii) Flow Cytometry

This operation must also be carried out using as little illumination as possible to prevent photo-bleaching. At least 10,000 cells are required for this procedure, an optimum number is 100,000–200,000. A sample of untransfected cells is also required for comparison.

The transfected HL-60 cells were washed with 0.2 $\mu$l of filtered PBS using a microcentrifuge set at low speed. After the final wash the cells were re-suspended in 100 $\mu$l PBS. Analysis was carried out using standard flow cytometry methods. Cells transfected with pEGFP-C1 vector showed a clear increase in peal channel and mean over control cells, indicating that they were fluorescent and had thus been transfected.

Example 3

Transfection Using Depressurisation

HL-60 cells were suspended in an aqueous medium comprising EBSS and having an osmolarity of approximately 300 mOsm. The medium contained approximately 500,000 cells/ml and either fluorescently labelled bovine serum albumin (FITC-BSA) or rhodamine-dextran, at a concentration of 3.0 $\mu$g/ml. The suspension of HL-60 cells was transferred to a sterile tube and placed in a pressure chamber. A nitrogen cavitation bomb was employed as a pressure chamber. The pressure of the chamber was increased to $3 \times 10^6$ Pa (30 Barr) for 10 minutes, after which time the pressure was released. The cells were analysed by fluorescence microscopy.

Analysis of Transfected Suspension Cells (i) Confocal Microscopy

This operation needs to be performed using as little illumination as possible, to prevent photo-bleaching.

The transfected cells were washed twice with PBS (phosphate buffered saline). The cells (approx. $1 \times 10^4$ in number) were re-suspended in 20 $\mu$l PBS and placed in the wells of a poly-L-lysine coated microscope slide. The cells were then allowed to settle for 20 mins.

The PBS was then gently removed and PFA (paraformaldehyde) was added (4%, 20 $\mu$l). The cells were left to be fixed for 20 mins. Then, the PFA was gently removed and 15 µl of DABCO (1,4-diazabicyclo[2,2,2] octane) was added. A coverslip was placed over the cells and sealed with grease.

The analysis was performed under a microscope according to standard confocal microscopy techniques. The HL-60 cells transfected with FITC-BSA and rhodamine-dextran exhibited clear fluorescence present inside the cells, not at the cell surface. Thus the cells were successfully transfected. Greater than 90% transfection was achieved, with cell death being less than 10%.

(ii) Flow Cytometry

This operation must also be carried out using as little illumination as possible to prevent photo-bleaching. At least 10,000 cells are required for this procedure, an optimum number is 100,000–200,000. A sample of untransfected cells is also required for comparison.

The transfected HL-60 cells were washed with 0.2 µl of filtered PBS using a microcentrifuge set at low speed. After the final wash the cells were re-suspended in 100 µl PBS. Analysis was carried out using standard flow cytometry methods. Cells transfected with FITC-BSA and rhodamine-dextran showed a clear increase in peal channel and mean over control cells, indicating that they were fluorescent and had thus been transfected.

What is claimed is:

1. A method for introducing a substance into a cell, which method comprises:
   (a) generating bubbles of a gas in a liquid medium comprising the cell, the bubbles being capable of forming a hole in the surface of the cell when one or more bubbles interact with the cell, wherein the bubbles of gas are generated by a step selected from the group consisting of sparging, a chemical reaction, an electrochemical reaction and depressurisation, and if the bubbles of gas are generated by sparging, the radius of the bubbles is from one third to five times the radius of the cell; and
   (b) introducing the substance into the cell.

2. A method according to claim 1, wherein the substance is a hydrophilic substance.

3. A method according to claim 1, wherein the substance is a compound having a molecular weight of 100 or more.

4. A method according to claim 1, wherein the substance is a substance selected from the group consisting of nucleic acid, a protein, a hormone, a polysaccharide, a dye, and a drug.

5. A method according to claim 1, wherein the cell is an animal cell.

6. A method according to claim 1, wherein the cell is a protoplast derived from a cell having a cell wall.

7. A method according to claim 1, wherein the cell is a member of a population of cells.

8. A method according to claim 7, wherein the population of cells is in the form of a cell suspension, or is in the form of adherent cells.

9. A method according to claim 1, wherein the bubbles of gas are generated by passing a gas through the liquid medium.

10. A method according to claim 1, wherein the bubbles of gas are generated by depressurisation of the liquid medium.

11. A method according to claim 1, wherein the bubbles of gas are generated by a means selected from the group consisting of a chemical means and an electrochemical means.

12. A method according to claim 1, wherein the bubbles are generated and periodically in two or more pulses.

13. A method according to claim 12, wherein the duration of the pulses is controlled by a programmable means.

14. A kit for introducing a substance into a cell, which kit comprises:
   (i) a means for generating bubbles of a gas in a liquid by a step selected from the group consisting of sparging, a chemical reaction, an electrochemical reaction and depressurisation, wherein the bubbles have dimensions substantially sufficient to form a hole in the surface of the cell when one or more bubbles interact with the cell, and if the means for generating bubbles is a sparging means, the radius of the bubbles is from one third to five times the radius of the cell; and
   (ii) a liquid medium.

15. A method for introducing a substance into a cell, which method uses an apparatus comprising:
   (a) a container for holding a liquid medium comprising the cell; and
   (b) a means for generating bubbles of a gas in the liquid medium by a step selected from the group consisting of sparging, a chemical reaction, an electrochemical reaction and depressurisation.

16. A method according to claim 15, wherein the means for generating bubbles of gas in the liquid medium comprises a means for passing gas through the liquid medium, the means comprising a filter system comprising a filter layer formed from glass, a filter layer formed from polypropylene and a filter layer formed from cellulose nitrate.

* * * * *